United States Patent
Min

(10) Patent No.: US 12,268,886 B2
(45) Date of Patent: Apr. 8, 2025

(54) METHOD AND SYSTEM FOR MONITORING TYPES OF CAPTURE OF A LEADLESS IMPLANTABLE MEDICAL DEVICE

(71) Applicant: PACESETTER, INC., Sylmar, CA (US)

(72) Inventor: Xiaoyi Min, Camarillo, CA (US)

(73) Assignee: Pacesetter, Inc., Sylmar (CA)

(*) Notice: Subject to any disclaimer, the term of this patent is extended or adjusted under 35 U.S.C. 154(b) by 554 days.

(21) Appl. No.: 16/388,625

(22) Filed: Apr. 18, 2019

(65) Prior Publication Data

US 2020/0330771 A1 Oct. 22, 2020

(51) Int. Cl.
| | |
|---|---|
| *A61N 1/37* | (2006.01) |
| *A61B 5/00* | (2006.01) |
| *A61N 1/05* | (2006.01) |

(52) U.S. Cl.
CPC ............ *A61N 1/3712* (2013.01); *A61B 5/686* (2013.01); *A61N 1/0504* (2013.01); *A61N 1/056* (2013.01); *A61N 1/3702* (2013.01)

(58) Field of Classification Search
CPC .... A61N 1/3684; A61N 1/3712; A61N 1/371; A61N 1/3704; A61N 1/3702; A61N 1/39622; A61N 1/37; A61N 1/37288; A61N 1/3706; A61N 1/362; A61B 5/686; A61B 5/4836; A61B 5/7282; A61B 5/0031; A61B 5/0245; A61B 5/6869
See application file for complete search history.

(56) References Cited

U.S. PATENT DOCUMENTS

| | | | |
|---|---|---|---|
| 9,254,392 B2* | 2/2016 | Ghosh | .................... A61N 1/371 |
| 2018/0036547 A1* | 2/2018 | Reddy | ................ A61N 1/39622 |

* cited by examiner

*Primary Examiner* — Deborah L Malamud
(74) *Attorney, Agent, or Firm* — Dean D. Small; The Small Patent Law Group, LLC

(57) ABSTRACT

A computer implemented method and system for monitoring types of capture within a distributed implantable system having a leadless implantable medical device (LIMD) to be implanted entirely within a local chamber of the heart and having a subcutaneous implantable medical device (SIMD) to be located proximate the heart are provided. The method is under control of one or more processors of the SIMD configured with program instructions. The method collects far field (FF) evoked cardiac signals following the pacing pulses delivered by the LIMD for an event and analyzes the FF evoked cardiac signals to identify a type of HIS capture as loss of capture (LOC), selective capture, myocardial tissue-only (MT-only) capture, or a non-selective (NS) capture and records a label for the event based on the type of HIS capture identified.

33 Claims, 7 Drawing Sheets

METHOD AND SYSTEM FOR MONITORING TYPES OF CAPTURE OF A LEADLESS IMPLANTABLE MEDICAL DEVICE

BACKGROUND

Currently, subcutaneous implantable medical devices (SIMD) are provided for a variety of cardiac applications. The SIMD includes a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker, cardioversion and/or defibrillation functionality.

Recently, small sized devices have been proposed for intra-cardiac implant within the heart. These devices, termed leadless pacemakers or leadless implantable medical devices (LIMDs), are typically characterized by the following features: the LIMD is devoid of leads that pass out of the heart to another component, such as a pacemaker CAN outside of the heart; the LIMD includes electrodes that are affixed directly to the housing of the device; the entire device is attached to the heart; and the device is capable of pacing and sensing in the chamber of the heart where implanted.

Further, current leadless IMD are not able to automatically determine capture thresholds. More specifically, the conventional LIMD is unable to implement an automated search through various pacing thresholds to determine a pacing voltage that achieves capture of local tissue. For example, in order to have similar auto-capture algorithms as in traditional pacemakers, it can necessitate minimizing blanking and recharge time, and also achieving low polarization, in the leadless pacemaker to enable automatic search for a capture threshold. Accordingly, a need remains for methods and systems to reliably sense physiologic behavior of the heart and provide appropriate therapies using a leadless system, including detecting and managing the capture thresholds of leadless pacemakers.

SUMMARY

In accordance with embodiments herein, a computer implemented method for monitoring types of capture within a distributed implantable system having a leadless implantable medical device (LIMD) to be implanted entirely within a local chamber of the heart and having a subcutaneous implantable medical device (SIMD) to be located proximate the heart is provided. The method is under control of one or more processors of the SIMD configured with program instructions. The method collects far field (FF) evoked cardiac signals following the pacing pulses delivered by the LIMD for an event and analyzes the FF evoked cardiac signals to identify a type of HIS capture as loss of capture (LOC), selective capture, myocardial tissue-only (MT-only) capture, or a non-selective (NS) capture and records a label for the event based on the type of HIS capture identified.

Optionally, the method may utilize the SIMD for obtaining FF baseline cardiac signals and may analyze the FF baseline cardiac signals to identify baseline characteristics of interest (COI). The analyzing may comprise identifying the type of HIS capture based on the baseline COI and capture-indicative COI of the FF evoked cardiac signals. The analyzing may comprise comparing a baseline width of a QRS complex with a QRS width of the FF evoked cardiac signals and may compare a baseline level of activity in the isoelectric interval with a level of activity in the isoelectric interval of the FF evoked cardiac signals. The method may label the event as MT-only capture indicating that the pacing pulses from the LIMD captured myocardial tissue only.

Optionally, the analyzing may comprise comparing a baseline width of a QRS complex with a QRS width of the FF evoked cardiac signals and may compare a baseline AR interval to an AR interval of the FF evoked cardiac signals. The method may label the event as LOC indicating that the pacing pulses from the LIMD did not capture the HIS bundle or myocardial tissue. The analyzing may comprise comparing a baseline width of a QRS complex with a QRS width of the FF evoked cardiac signals and may compare a baseline level of activity in the isoelectric interval with a level of activity in the isoelectric interval of the FF evoked cardiac signals. The method may label the event NS capture indicating that the pacing pulses from the LIMD captured the HIS bundle and myocardial tissue. The analyzing may comprise comparing a baseline width of a QRS complex with a QRS width of the FF evoked cardiac signals and may compare a baseline AR interval to an AR interval of the FF evoked cardiac signals and, based thereon, may label the event as selective capture indicating that the pacing pulses from the LIMD captured the HIS bundle only.

Optionally, the method may bin the labels for a plurality of the events and determine when a pre-selected criteria of the events labeled with LOC is met. The method may transmit LOC information from the SIMD to the LIMD and based on the determining, may initiate an auto threshold search. The LIMD may deliver pacing pulses according to a pacing parameter search scheme. The SIMD may determine the type of HIS capture for corresponding evoked FF cardiac signals. The method may transmit the capture state information from the SIMD to the LIMD and based on the capture state information, the LIMD may update a pacing parameter. The SIMD may collect the FF cardiac signals along primary and secondary sensing vectors extending between a case electrode and sensing sites along at least one parastemal lead.

In accordance with embodiments herein, a system for monitoring types of capture within a distributed implantable system having a leadless implantable medical device (LIMD) to be implanted entirely within a local chamber of the heart and having a subcutaneous implantable medical device (SIMD) to be located proximate the heart is provided. The system includes at least one processor. A memory is coupled to the at least one processor. The memory stores program instructions. The program instructions are executable by the at least one processor of the SIMD to collect far field (FF) evoked cardiac signals following the pacing pulses delivered by the LIMD for an event, analyze the FF evoked cardiac signals to identify a type of HIS capture as loss of capture (LOC), selective capture, myocardial tissue-only (MT-only) capture, or a non-selective (NS) capture and record a label for the event based on the type of HIS capture identified.

Optionally, the program instructions may be further executable by the at least one processor to utilize the SIMD to obtain FF baseline cardiac signals and analyze the FF baseline cardiac signals to identify baseline characteristics of interest (COI). The program instructions may be further executable by the at least one processor to utilize the SIMD to analyze the FF evoked cardiac signals to identify the type of HIS capture based on the baseline COI and capture indicative COI. The program instructions may be further executable by the at least one processor to compare a baseline width of a QRS complex with a QRS width of the FF evoked cardiac signals and may compare a baseline level of activity in the isoelectric interval with a level of activity in the isoelectric interval of the FF evoked cardiac signals, and based thereon, may label the event as MT-only capture indicating that the pacing pulses from the LIMD captured myocardial tissue only.

Optionally, the program instructions may be further executable by the at least one processor to compare a baseline width of a QRS complex with a QRS width of the FF evoked cardiac signals and may compare a baseline AR interval to an AR interval of the FF evoked cardiac signals, and based thereon, may label the event as LOC indicating that the pacing pulses from the LIMD did not capture the HIS bundle or myocardial tissue. The program instructions may be further executable by the at least one processor to compare a baseline width of a QRS complex with a QRS width of the FF evoked cardiac signals and may compare a baseline level of activity in the isoelectric interval with a level of activity in the isoelectric interval of the FF evoked cardiac signals, and based thereon, may label the event NS capture indicating that the pacing pulses from the captured the HIS bundle and myocardial tissue.

Optionally, the program instructions may be further executable by the at least one processor to compare a baseline width of a QRS complex with a QRS width of the FF evoked cardiac signals and may compare a baseline AR interval to an AR interval of the FF evoked cardiac signals, and, based thereon, may label the event as selective capture indicating that the pacing pulses from the LIMD captured the HIS bundle only. The program instructions may be further executable by the at least one processor to utilize the SIMD to bin the labels for a plurality of the events and determine when a pre-selected criteria of the events labeled with LOC is met. The processor may transmit LOC information from the SIMD to the LIMD and based on the determine, cause the LIMD to initiate an auto threshold search.

The program instructions may further executable by the at least one processor to utilize the LIMD to deliver pacing pulses according to a pacing parameter search scheme and may utilize the SIMD to determine type of HIS capture for corresponding evoked FF cardiac signals. The processor may utilize the SIMD to transmit the capture state information from the SIMD to the LIMD and based on the capture state information, may determine a pacing parameter. The program instructions may be further executable by the at least one processor to utilize the SIMD to collect the FF cardiac signals along primary and secondary sensing vectors extending between a case electrode and sensing sites along at least one parastemal lead.

DETAILED DESCRIPTION

Figure 1A:
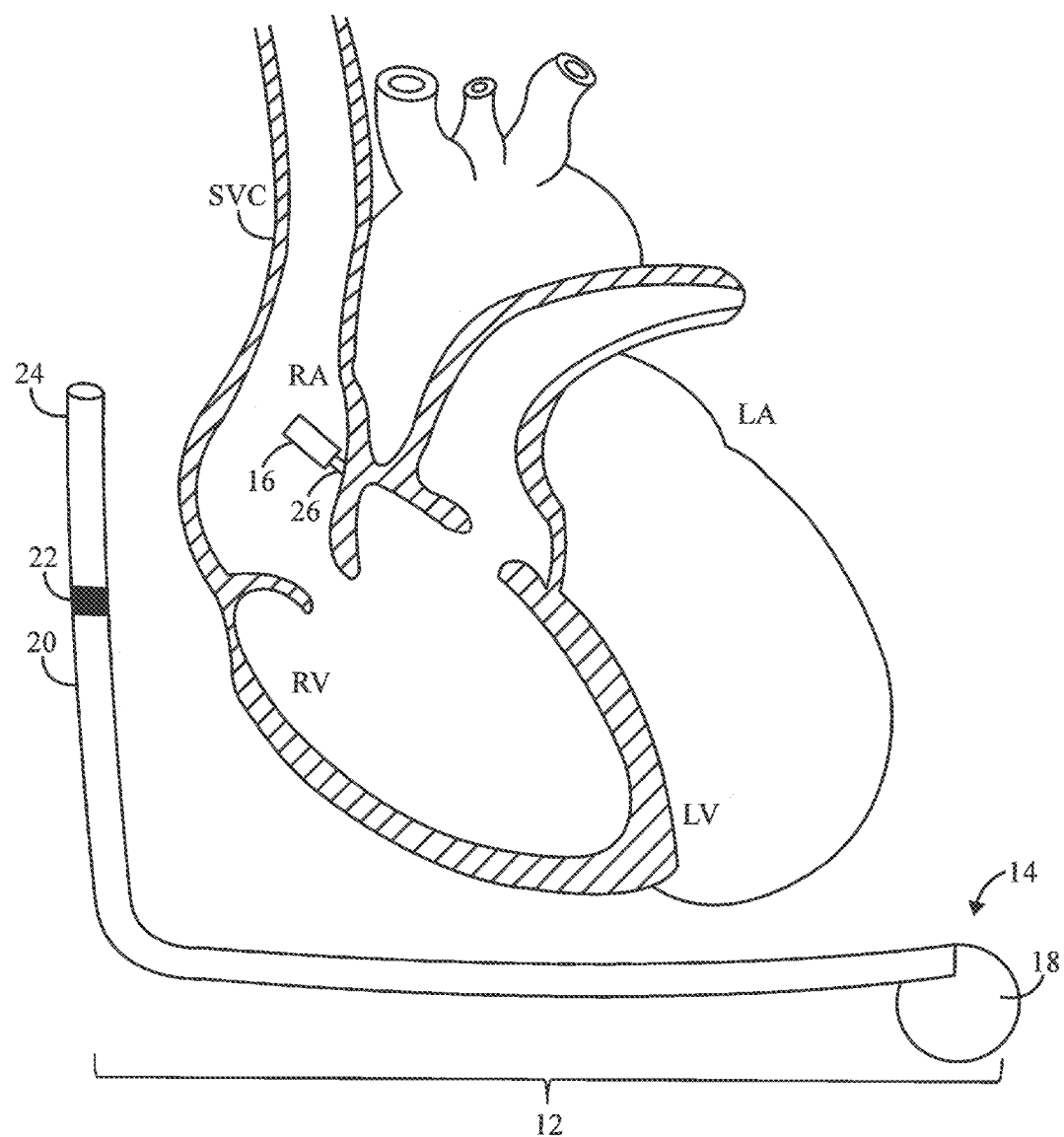
FIG. 1A illustrates a graphical representation of a heart with an implantable medical system to provide pacing therapy, cardiac resynchronization therapy (CRT) as well as general arrhythmia therapy in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Terms

The term "HIS bundle pacing" shall refer to use of a HIS pacing lead at a selected location for capturing the HIS bundle and includes types of HIS pacing capture such as selective capture, myocardial tissue-only capture, non-selective capture, loss of capture, and the like.

The term "selective capture" shall mean that a corresponding pacing pulse from the LIMD only captured the HIS bundle and did not capture myocardial tissue.

The terms "myocardial tissue-only capture" and "MT-only capture" shall mean that a corresponding pacing pulse from the LIMD only captured myocardial tissue and did not capture the HIS bundle.

The terms "non-selective capture" and "NS capture" shall mean that the corresponding pacing pulse captured both the HIS bundle and the myocardial tissue.

The terms "loss of capture" and "LOC" shall mean that a corresponding pacing pulse from the LIMD failed to capture the HIS bundle and myocardial tissue. When loss of capture occurs, the corresponding pacing pulse does not achieve any of selective capture, MT-only capture and/or NS capture.

The terms "type of HIS capture" and "capture state" shall mean an extent to which a pacing pulse achieves selective capture, MT-only capture, non-selective capture, or LOC. The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, iii) receiving the data, signals, information, etc. over a communications link between the LIMD and the SIMD, and/or iv) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of an LIMD and/or a SIMD, may include receiving the data, signals, information, etc. over an i2i communication link from another IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

Overview

In accordance with embodiments herein, methods and systems are provided herein to reliably sense physiologic behavior of the heart and provide appropriate therapies utilizing a leadless system. Embodiments herein avoid certain difficulties in implementing a leadless implantable medical device (LIMD) that self-manages signal capture such as conflicting restraints on size, power constraints, electrode performance, and processing requirements.

In accordance with embodiments herein, the sensing electrodes of a subcutaneous implantable cardiac device (SIMD) may be used to discriminate paced beats and monitor the capture state of a LIMD such as by collecting and analyzing far field (FF) cardiac signals following the pacing pulses delivered by the LIMD. The systems and methods described herein may be implemented with either traditional pacing in the ventricle or atrium or HIS bundle pacing. The SIMD may record a label for the event based on analysis of the FF cardiac signals and bin the labels for a plurality of the events. The SIMD may further transmit at least a portion of the binned information from the SIMD to the LIMD upon reaching a predetermined criteria. Based on the information received from the SIMD, the LIMD may initiate a process to alter its operational parameters, such as an auto-threshold search or the like. At each paced event of the LIMD, the SIMD determines the type of capture or LOC.

Embodiments may be implemented in connection with one or more implantable medical devices (IMDs). Non-limiting examples of IMDs include a cardiac monitoring device, pacemaker, cardioverter, cardiac rhythm management device, defibrillator, leadless monitoring device, leadless pacemaker and the like. For example, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device and Method Including the Same", which are hereby incorporated by reference. Additionally, or alternatively, the IMD may include one or more structural and/or functional aspects of the device(s) described in U.S. Pat. No. 9,232,485 "System and Method for Selectively Communicating with An Implantable Medical Device", which is hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parastemal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entiretles. Further, one or more combinations of IMDs may be utilized from the above incorporated patents and applications in accordance with embodiments herein.

Communication between the LIMD and SIMD can be accomplished through i2i communications methods as described in one or more of U.S. Pat. No. 10,182,765, titled "Systems and methods for classifying signals of interest in a cardiac rhythm management device", U.S. Pat. No. 10,173,068 titled "Mitigating false messaging in leadless dual-chamber pacing systems and other IMD systems", U.S. Pat. No. 10,052,491, titled "Mitigating false messaging in leadless dual-chamber pacing systems and other IMD systems", U.S. Pat. No. 9,561,382 titled "System and method for low power communication between implantable devices", and U.S. Pat. No. 9,522,280, titled "Leadless dual-chamber pacing system and method", which are hereby incorporated by reference in their entireties.

LIMD and SIMD

FIG. 1A illustrates a graphical representation of a heart with an implantable medical system 12 to provide pacing therapy, cardiac resynchronization therapy (CRT) as well as general arrhythmia therapy. The system 12 includes a first leadless implantable medical devices (LIMD) 16 configured to be implanted entirely within the heart. The system 12 also includes a subcutaneous implantable medical device (SIMD) 14 configured to be implanted in a subcutaneous area exterior to the heart.

In the example of FIG. 1A, the LIMD 16 is implanted proximate the HIS bundle. Optionally, additional LIMDs may be implanted in one or more of the right atrium, right ventricle. the left atrium, and the left ventricle. Alternatively, the LIMD 16 may be implanted in other chambers and/or other positions exterior to the heart. For example, the LIMD 16 may be implanted in the right ventricle, right atrium, left ventricle, left atrium, the pericardial sac, or in one of the great cardiac veins. Optionally, more than one LIMD 16 may be utilized with each LIMD 16 positioned in a different chamber of the heart, the pericardial sac and/or in one of the great cardiac veins. The LIMD 16 is configured to deliver various therapies, such as pacing therapy, antitachycardia pacing therapy, and the like.

In the example of FIG. 1A, the SIMD 14 is positioned in a subcutaneous area. The SIMD may be, for example and without limitation, a subcutaneous implantable cardioverter-defibrillator. The SIMD is a device that does not require insertion of a transvenous lead. Rather, the SIMD includes subcutaneous pulse generator that may be implanted in the left lateral chest and a subcutaneous left parastemal lead-electrode. Optionally, the SIMD 14 may be positioned in a different subcutaneous area, such as proximate the lower apex of the left ventricle and/or right ventricle. The SIMD 14 is configured to deliver various arrhythmia therapies, such as pacing therapy, antitachycardia pacing therapy, cardioversion therapy, defibrillation therapy and the like. Optionally, the LIMD 16 and SIMD 14 may deliver the same or different types of therapies, based upon device longevity, energy storage, and other design characteristics.

The SIMD 14 includes a housing 18 having a header configured to be connected to a lead 20. The lead 20 includes one or more electrodes 22, 24 positioned along a length thereof. The housing 18 is also configured to operate as an electrode. The electrodes 22, 24 and the housing 18 are configured to perform sensing (along one or more sensing vectors) and to deliver various types of therapy. The lead 20 is positioned such that the electrodes 22 and 24 are positioned proximate (but outside of) various regions or chambers of the heart. In the example of FIG. 1, the SIMD 14 is positioned proximate the apex of the LV, while the electrode 22 is positioned at an intermediate point along the LV and the electrode 24 is positioned proximate the LA. Optionally, the SIMD 14 and lead 20 may be positioned in alternative locations and include alternative numbers of electrodes. Optionally, the SIMD 14 may be configured to operate without any lead 20 connected thereto. For example, the housing 18 of the SIMD 14 may include one or more electrically separate electrodes, where one combination of electrodes cooperates to perform sensing and the same or a different combination of electrodes cooperates to deliver therapy.

The LIMD 16 has a housing with a proximal end 26 that is configured to engage local tissue in the right ventricle. Electrodes (not illustrated in FIG. 1) may be located along the housing at various positions and combinations, such as, for example and without limitation, at the distal end and the proximal end 26 of the housing. The internal electrical components and electrodes may be implemented as described in U.S. Publication No. 2014/0107723, and in U.S. application Ser. No. 15/067,054, entitled "Method and System to Determine Capture Thresholds", which are expressly incorporated herein by reference in their entirety.

The distributed system 12 has one or more LIMDs 16 and one or more SIMDs 14 that operate as separate therapy delivery devices. The LIMD 16 and SIMD 14 include at least two types of sensing configurations, namely a cardiac event sensing channel tuned to detect intrinsic and/or paced cardiac events. For example, the cardiac event sensing channel, for an atrial pacing device, may be tuned and function to sense P-waves or paced events delivered in the atrium. A ventricular pacing device may be tuned and function to sense R-waves or paced events delivered in the ventricle over the cardiac event sensing channel.

Figure 1B:
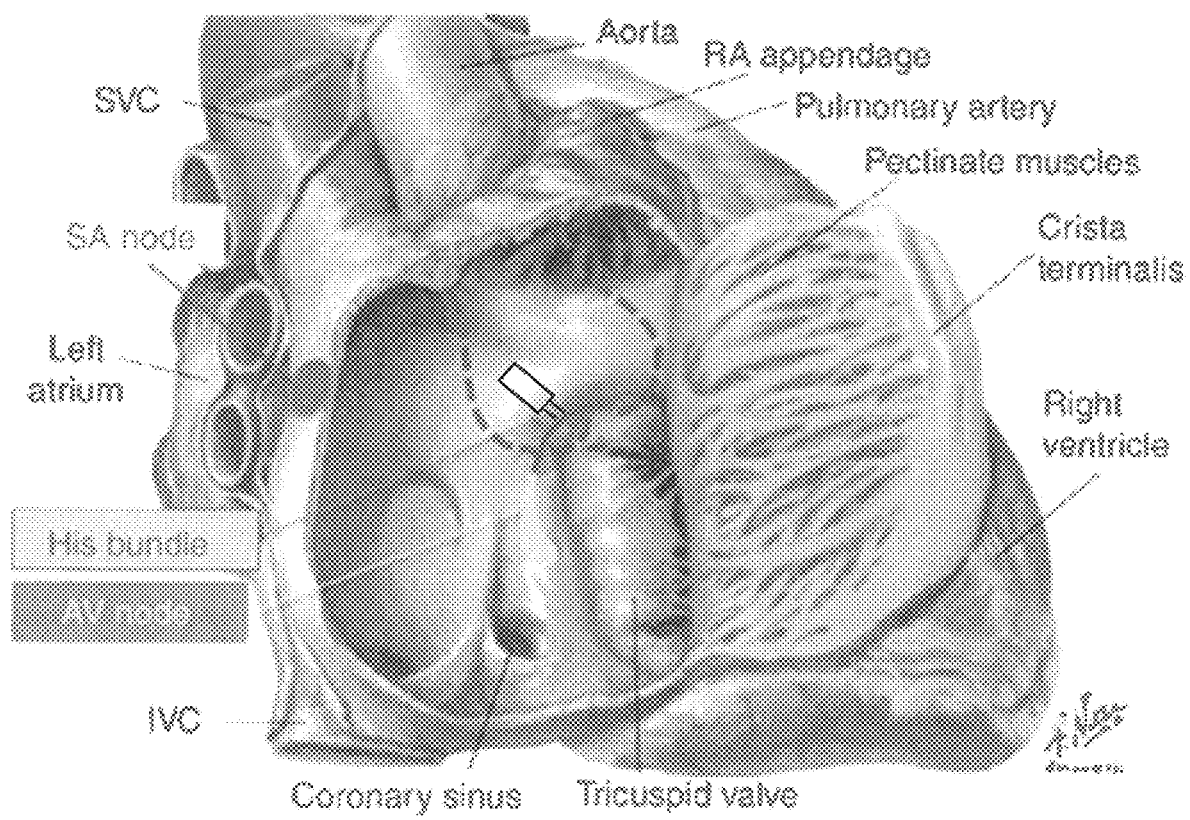
FIG. 1B illustrates a model of a heart rotated to illustrate the LIMD from an alternative view in accordance with embodiments herein.

FIG. 1B illustrates a model of a heart rotated to illustrate the LIMD 16 from an alternative view. The LIMD 16 is implanted in heart tissue proximate the HIS bundle. Additionally, or alternatively, the LIMD 16 can be implanted under the valve inside of the right ventricle. The LIMD 16 is configured to deliver pacing pulses that have pacing parameters set to achieve HIS bundle pacing. As explained herein, the SIMD 14 is utilized to track the type of capture achieved by the LIMD 16, and to facilitate to implementation of an auto-capture search for a pacing threshold appropriate to achieve HIS bundle pacing.

Figure 2:
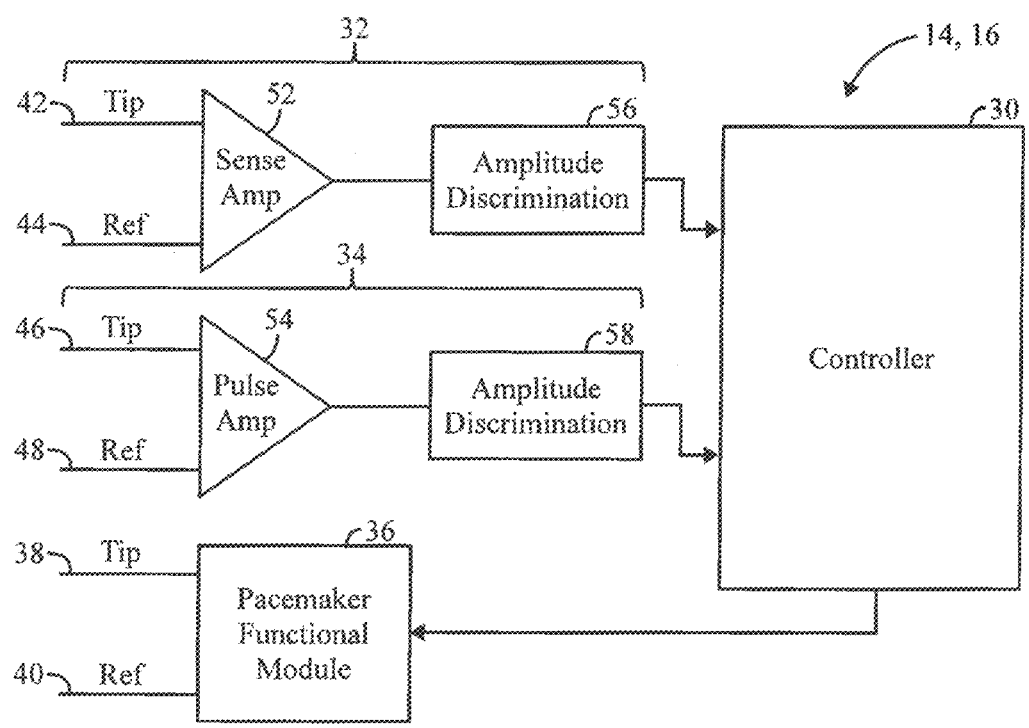
FIG. 2 illustrates a simple block diagram of at least a portion of the circuitry within an LIMD and SIMD in accordance with embodiments herein.

FIG. 2 illustrates a simple block diagram of at least a portion of the circuitry within an LIMD 16 and SIMD 14. The SIMD 14 and LIMD 16 each include a controller 30 that is coupled to cardiac sensing circuitry 32 and pulse sensing circuitry 34. The controller 30 also utilizes or communicates with various other electronic components, firmware, software and the like that generally perform sensing and pacing functions (as generally denoted by a pacemaker functional block 36). The cardiac sensing circuitry 32 and 34 are configured to detect intrinsic and paced cardiac events. The sensing circuitry 32 and 34 may be tuned in different manners based upon various characteristics, such as whether the sensing circuitry 32, 34 is listening for a near field (NF) or far field (FF) signals and the nature of the signal being sensed (e.g., a far field cardiac signal, a far field event marker, a near field cardiac signal, a near field event marker).

The controller 30 is configured to analyze incoming intrinsic and/or paced cardiac events (as sensed over the cardiac sensing circuitry 32). Based on this analysis, the controller 30 in the LIMD 16 performs various pacemaker related actions, such as setting or ending timers, recording data, delivery of therapy and the like. The controller 30 of the SIMD 14 performs various cardioversion/defibrillation related functions. Inputs 38 and 40 represent output terminals that are coupled through a switching circuit (in the functional module 36) to corresponding electrodes on the housing of the LIMD 16 and/or lead/housing of the SIMD 14.

Inputs 42-48 are provided to the cardiac and pulse sensing circuitry 32 and 34. By way of example, with reference to LIMD 16, inputs 42 and 44 may be coupled to tip and reference electrodes that supply sensed signals to a sensing amplifier 52. Inputs 46 and 48 may be coupled to the same or different tip and reference electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. With reference to the SIMD 14, the inputs 42 and 44 may be coupled to various combinations of the electrodes 22, 24 and the electrode formed by the housing 18.

By way of example, the sensing amplifier 52 and discriminator 56 may be tuned to perform NF or FF sensing and have programmable or automatic blanking periods. The blanking period is set to avoid sensing unwanted events at the sensing amplifier 52. For example, when the LIMD 16 represents a ventricular device, the sensing amplifier 52 and discriminator 56 may be tuned or configured to sense R-waves occurring in the local ventricle. Hence, the sensing amplifier 52 may be programmed to a select gain, while the discriminator 56 is programmed to only pass signals that exceed a select sensing threshold. Optionally, the discriminator 56 may include a band pass, low pass or high pass filter set to only pass signals within a select frequency range. The sensing amplifier 52 and/or discriminator 56 may have a low pass frequency (e.g., 10-120 Hz). The gain, threshold and/or pass band may be adjusted for atrial versus ventricular devices.

The pulse amplifier 54 and amplitude discriminator 58 are configured to detect select communications pulses having one or more known predetermined formats. For example, the gain of the pulse amplifier 54 and threshold of the discriminator 58 may be set to pass only signals below a select pulse maximum threshold and/or pulses having a select duration. Optionally, the discriminator 58 may include a band pass, low pass or high pass filter set to only pass pulses within a select frequency range. The pulse amplifier 54 and/or discriminator 58 may have a high pass frequency (e.g., 500 Hz-10 KHz). The pulse amplifier 54 and amplitude discriminator 58 may also be configured to sense pacing pulses delivered in the local and/or remote chambers. The communications pulses sensed by the pulse amplifier 54 and amplitude discriminator 58 represent event markers that are delivered to the controller 30 and used to indicate different events of interest (e.g., physiologic and non-physiologic events or actions). As explained herein, the controller 30 then takes appropriate action, depending upon the situation.

Optionally, a single amplifier may be used in place of amplifiers 52 and 54, thereby detecting low and high frequency signals. An output of the single amp may be coupled to a low pass filter in parallel with a high pass filter that separate the low and high frequency components, respectively, namely the cardiac events and the communications pulses.

As used throughout, the terms "near field", "far field", "local" and "remote" shall be used from the perspective of the LIMD 16. Accordingly, the LIMD 16 will sense local events of interest in the near field that occur in the local chamber, in which the LIMD 16 is implanted. As an example, when the LIMD 16 is implanted in a ventricle, the local chamber constitutes the corresponding ventricle, and the near field corresponds to the same ventricle, while the far field corresponds to one or both atrium and may represent the opposite ventricle. The SIMD 14 (and sensing electrodes) are located outside of the heart and accordingly, the cardiac signals sensed by the SIMD 14 are not readily characterized as near field or far field relative to the SIMD. Also, the SIMD 14 is not readily characterized to have a local chamber or a remote chamber. Instead the SIMD 14 senses signals in the "far field" of the LIMD 16 and, from the perspective of the LIMD 16.

HIS Auto-Capture Detection Process

Figure 3A:
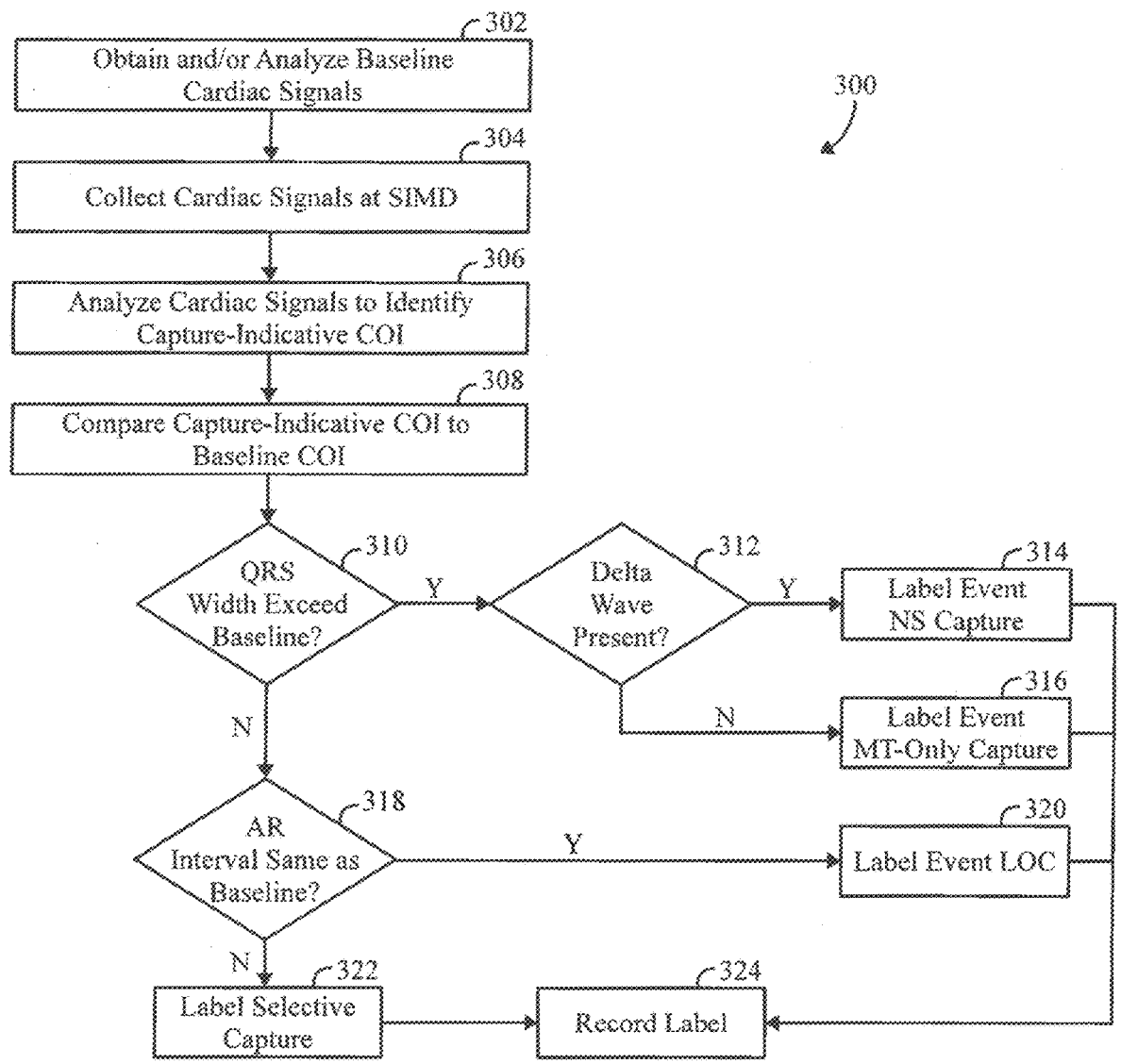
FIG. 3A illustrates a computer-implemented method for monitoring types of capture in accordance with embodiments herein.

FIG. 3A illustrates a computer-implemented method 300 for monitoring types of capture in accordance with embodiments herein. FIG. 3A illustrates monitoring types of capture for patients exhibiting a normal or narrow QRS width, but the same principles illustrated herein are applicable to monitor loss of capture for patients exhibiting a wider-than-normal QRS width. It should be recognized that while the operations of method 300 are described in a somewhat serial manner, one or more of the operations of method 300 may be continuous and/or performed in parallel with one another. For example, the various operations performed by the LIMD may be continuous and performed in parallel with the operations performed by the SIMD, and vice versa. The SIMD and LIMD may both collect and analyze cardiac signals for common cardiac beats in connection with identifying arrhythmias and delivering therapies in connection therewith. Alternatively, the SIMD may identify and treat arrhythmias based on cardiac signals for beats that are collected entirely separate from the beats that are analyzed in connection with identifying the capture state of the LIMD (as described in FIG. 3). Optionally, the SIMD may utilize the cardiac signals for the same beats to detect and treat an arrhythmia, as well as to determine the capture state of the LIMD. Also, unless otherwise indicated, each operation of method 300 is performed under the control of one or more processors configured with program instructions.

The LIMD and SIMD are configured to be implanted, where the LIMD is implanted entirely within a local chamber of the heart and proximate to the HIS bundle. The LIMD is configured to deliver at least one type of therapy (e.g., a pacing therapy) within the local chamber. The SIMD is configured to be implanted proximate to the heart, but with electrodes outside of the heart (non-transvenous). The SIMD is configured sense ventricular arrythmia and deliver at least one other type of therapy (e.g., anti-tachycardia pacing (ATP), defibrillation, or other arrhythmia therapy). The LIMD and SIMD may deliver different or similar types of therapy (e.g., pacing, anti-tachycardia pacing, and the like). However, the SIMD may be able to provide additional therapy options not available on the LIMD due to size, power constraints, electrode positions and the like.

Beginning at 302, the one or more processors of the SIMD, obtain intrinsic far field (FF) baseline cardiac signals. For example, the one or more processors may direct sensing circuitry of the SIMD to collect the baseline cardiac signals. The baseline cardiac signals may be obtained at various points in time, such as at a time of implant, during physician clinic visits, at predetermined times of day (e.g., while sleeping), while the patient is in a predetermined state (e.g., exhibiting a select activity level, select heart rate, select postures) and the like. The one or more processors analyze the baseline cardiac signals to identify baseline characteristics of interest (COI), such as the width of the QRS complex, the AR interval, the amplitude of the R-wave peak, conduction delays to the SIMD sensing electrodes, the interval from sensed/paced atrial event to the QRS complex, the T-wave peak, the width of the ST segment, the morphology of the QRS complex and the like. Additionally, or alternatively, the one or more processors analyze the isoelectric interval between the sensed/paced atrial event (A/P-wave) and the intrinsic R-wave to determine a baseline level for the isoelectric interval as another baseline COI. Optionally, the one or more processors may obtain an ensemble of FF baseline cardiac signals and mathematically combine the ensemble of FF baseline cardiac signals, such as through averaging, mean, median, etc., to form a composite baseline cardiac signal. The one or more processors identify the baseline COI from the composite baseline cardiac signal.

As noted above, the operation at 302 may be performed at various times separate from, or in combination with, the remaining operations of FIG. 3 (as noted by the break in the arrow between 302 and 304).

Optionally, the one or more processors of the SIMD confirm that the LIMD is implementing a pacing therapy. The pacing therapy may be implemented in various manners based on the position, purpose, and functional capability of the LIMD. The SIMD may confirm the pacing therapy in various manners. For example, the SIMD may communicate one or more aspects of the SIMD functionality and/or therapy to the SIMD. Additionally, or alternatively, the confirmation may simply represent a basic hand-shake communication between the LIMD and SIMD to inform each device of the presence of the other. Additionally, or alternatively, the SIMD may be preprogrammed to assume the functionality of the LIMD, such that the "confirmation" is not a separate action. The LIMD may implement pacing functionality independent of the operations of the SIMD, such that the LIMD and SIMD do not time sense operations or delivery of therapy with one another. Additionally, or alternatively, the LIMD and SIMD may coordinate all or portions of sensing and/or therapy delivery with one another. For example, the SIMD and/or LIMD may transmit event and/or timing markers to one another to inform the other device of paced and/or sensed events At 304, the one or more processors of the SIMD direct sensing circuitry of the SIMD to collect cardiac signals. The cardiac signals may be collected continuously without coordinate, or regard for, a timing of the pacing therapy delivered by the LIMD. For example, the SIMD may be configured to deliver defibrillation therapy, cardioversion therapy, and the like. The SIMD collects cardiac signals in connection with arrhythmia monitoring and therapy to be provided by the LIMD. Additionally, or alternatively, the one or more processors of the LIMD may coordinate a time when the cardiac signals are collected with delivery of pacing pulses by the LIMD, such as when the LIMD and SIMD communicate with one another to coordinate therapy delivery therebetween. The cardiac signals collected by the SIMD generally represent far field cardiac signals as the cardiac signals are indicative of cardiac activity occurring in a chamber of the heart that is remote from the sensing electrodes (e.g., the SIMD electrodes are not in direct physical contact the either atria or ventricles of the heart).

At 306, the one or more processors of the SIMD analyze the current cardiac signals to identify capture-indicative COI therein. For example, the one or more processors analyze the current FF cardiac signals to identify, among other things, a paced atrial event (P-wave) and an intrinsic ventricular event (R-wave). Based on the P-wave and R-wave, the one or more processors identify one or more capture-indicative COI, such as the width of the QRS complex, a duration of the AR interval, and a presence/absence of delta waves in the isoelectric quiet interval (if HIS pacing is involved). Other COI include the amplitude of the R-wave peak, conduction delays to two or more sensing electrodes on the SIMD, the T-wave peak, the width of the ST segment, the morphology of the QRS complex, and the like.

Optionally, the one or more processors of the SIMD may obtain an ensemble of the cardiac signals over time and mathematically combine the ensemble of cardiac signals, such as through averaging, mean, median, etc., to form a composite cardiac signal. When a composite cardiac signal is utilized, the one or more processors identify the capture-Indicative COI(s) from the composite cardiac signal.

Next, at 308, the one or more processors of the SIMD compare the capture-indicative COI to corresponding baseline COI. The comparison includes comparing the capture-indicative COI to the baseline COI, that may be utilized as thresholds, in order to determine a type of HIS capture achieved by the LIMD. The one or more processors compare the baseline COI and capture-indicative COI for the width of the QRS complex, a duration of the AR interval, and a presence/absence of delta waves in the isoelectric quiet interval.

At 310, the one or more processors compare a width of the QRS complex (current capture-indicative COI) from the current FF cardiac signals with a baseline QRS width threshold (baseline COI). If the QRS complex width for the current FF cardiac signals exceeds the baseline QRS width threshold, the process interprets the condition to correspond to either an MT-only capture or NS capture, and flow moves to 312. If the QRS complex width for the current FF cardiac signals is the same as or less than the baseline QRS width threshold, the process interprets the condition to have a different type of HIS capture than MT-only capture or NS capture, and flow continues to 318.

At 312, the one or more processors compare the level of activity in the isoelectric interval (capture-indicative COI) of the current FF cardiac signal to the baseline level of activity (baseline COI) to search for delta waves. If the current level of activity exceeds the baseline level of activity by a predetermined amount, the process interprets the condition to indicate a presence of delta waves, and thus flow moves to 314. At 314, the one or more processors label the current beat/event to have a type of HIS capture that corresponds to non-selective (NS) capture. NS capture is indicated by the combination of capture-indicative COI conditions at 310 and 312. The NS capture label at 314 indicates that the pacing pulse from the LIMD captured the HIS bundle and captured the myocardial tissue. The NS capture label is then recorded at 324.

Alternatively, at 312, when the one or more processors determine that the current level of activity does not exceed the baseline level of activity, the process interprets this condition to indicate an absence of delta waves (or at least a relatively low level of delta waves), and thus flow moves to 316. At 316, the one or more processors label the current beat/event to have MT-only capture. The label designated at 316 indicates that the pacing pulse from the LIMD captured the myocardial tissue and did not capture the HIS bundle. The labeled MT-only capture event is then recorded at 324.

At 318, the one or more processors of the SIMD compare the current AR interval (current capture-indicative COI) between the P-wave and R-wave of the current FF cardiac signals to the baseline AR interval (threshold baseline COI). If the current AR interval is identical to, or within a select range of, the baseline AR interval, flow moves to 320. At 320, the one or more processors label the current beat/event to have LOC. The LOC label at 320 indicates that the pacing pulse from the LIMD did not capture the HIS bundle or the myocardial tissue. The LOC label is then recorded at 324.

Alternatively, at 318, if the current AR interval is the different from, or outside of a select range of, the baseline AR interval, flow moves to 322. At 322, the one or more processors label the current beat/event to have selective capture. The selective capture label at 322 indicates that that the pacing pulse from the LIMD captured the HIS bundle but did not capture the myocardial tissue. The selective capture label is then recorded at 324.

Figure 3B:
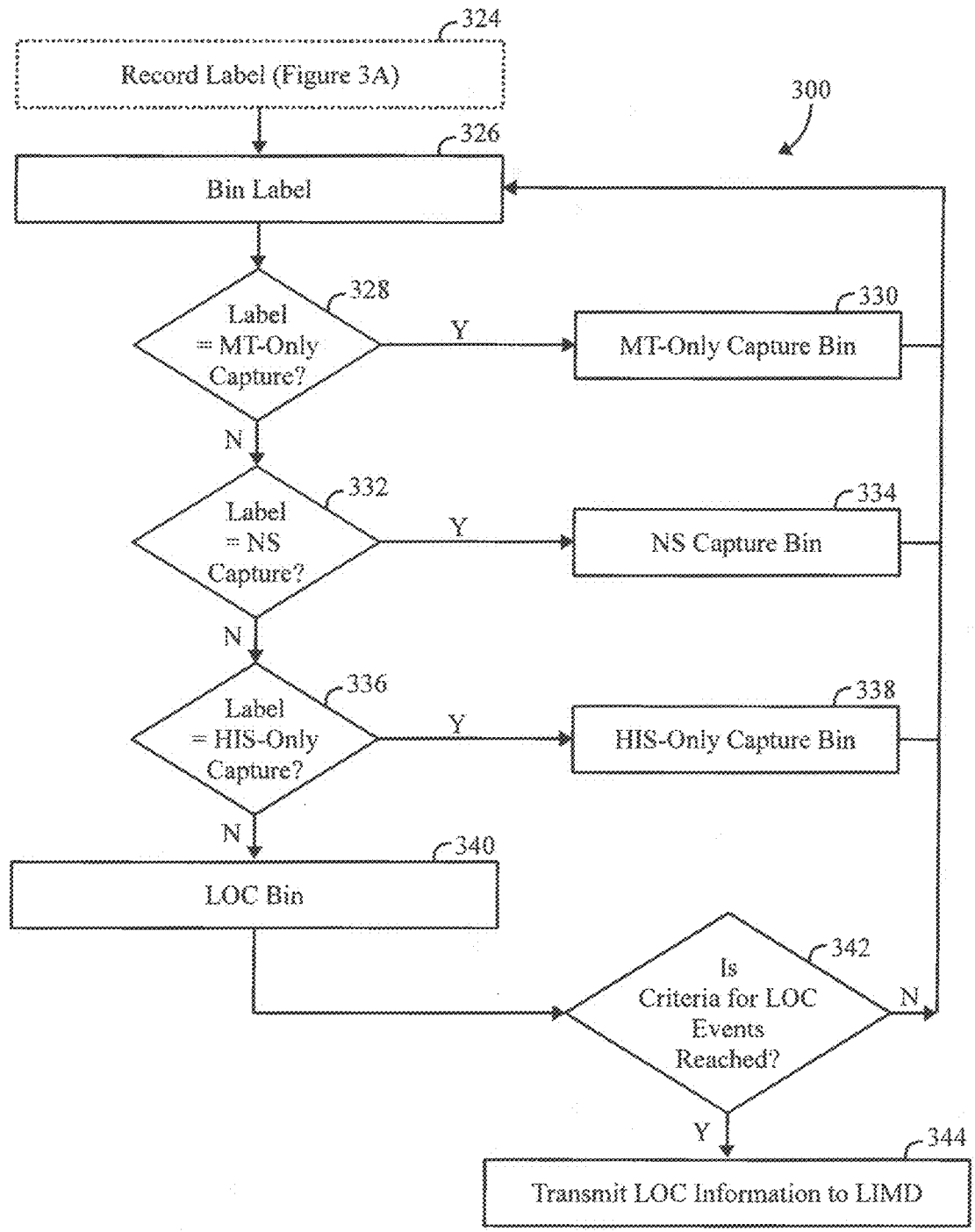
FIG. 3B illustrates a process for binning types of capture events in accordance with embodiments herein.
Figure 4A:
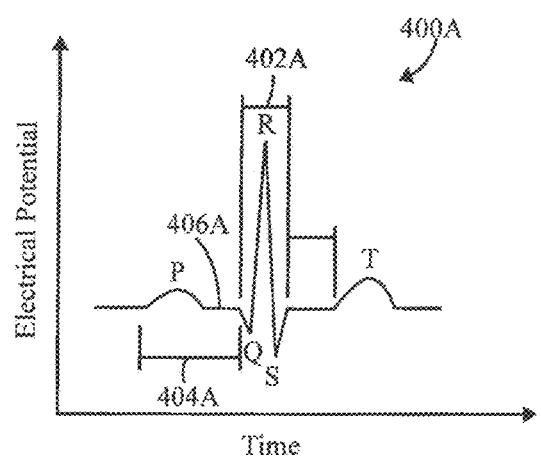
FIG. 4A illustrates a cardiac signal representative of a baseline cardiac signal in accordance with embodiments herein.

FIGS. 4A-4D illustrate examples of cardiac signals detected and analyzed in accordance with the methods of FIG. 3. FIG. 4A illustrates a cardiac signal representative of a baseline cardiac signal 400A normal or narrow QRS width. The baseline cardiac signal 400A can be analyzed to identify baseline COI such as, for example and without limitation, the baseline width of the QRS complex 402A, the baseline AR interval 404A, the baseline isoelectric interval 406A, and the like in order to establish corresponding baseline COI thresholds.

Figure 4B:
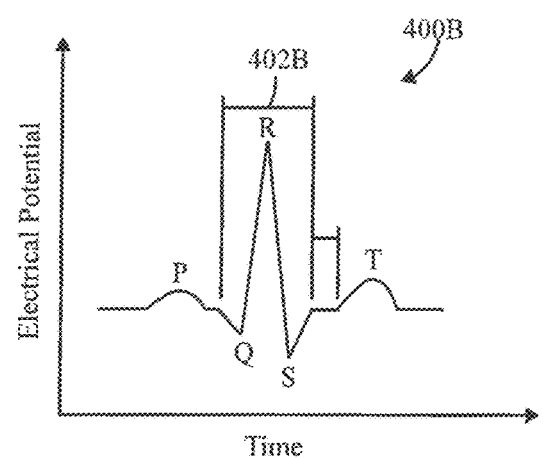
FIG. 4B illustrates a current cardiac signal representative of an MT-only capture beat/event in accordance with embodiments herein.

FIG. 4B illustrates a current cardiac signal 400B representative of an MT-only capture beat/event. The current cardiac signal 400B has a QRS complex width 402B that exceeds the baseline QRS width 402A threshold and a current level of activity of the isoelectric interval that does not exceed the baseline level of activity, indicating that the pacing pulses from the LIMD captured the myocardial tissue and did not capture the HIS bundle with HIS pacing.

With respect to the operations of FIG. 3A, the one or more processors of the SIMD collect and analyze the current cardiac signals 400A at 304, 306. The processors compare the current capture-indicative COI (QRS complex width 402) to the baseline COI (width 402A) at 306. At 310, the processors determine the width 402B exceeds the baseline COI width 402A and branches to 312. At 306, the processors compare the current capture-indicative COI (level of activity in the isoelectric interval 406D) to the baseline COI (the baseline level of activity of the isoelectric interval 406A). At 312, the processors determine that the current level of activity of the isoelectric interval does not exceed the baseline level of activity and branches to 316. At 316, the current cardiac signals 400B are labeled MT-only capture.

Figure 4C:
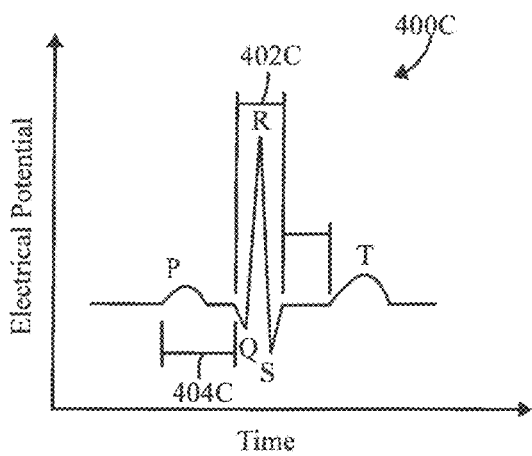
FIG. 4C illustrates a current cardiac signal representative of a LOC beat/event in accordance with embodiments herein.

FIG. 4C illustrates a current cardiac signal 400C representative of a LOC beat/event, where the current cardiac signal 400C has an AR interval 404C that is the same or within a select range of the baseline AR interval 404A threshold and a QRS complex having a width 402C that does not exceed the baseline QRS width 402A threshold, indicating that the pacing pulses from the LIMD did not capture the HIS bundle or the myocardial tissue.

With respect to the operations of FIG. 3A, the one or more processors of the SIMD collect and analyze the current cardiac signals 400C at 304, 306. The processors compare the current capture-indicative COI (QRS complex width 402C) to the baseline COI (width 402A) at 306. At 310, the processors determine the width 402C does not exceed the baseline COI width 402A and branches to 318. The one or more processors compare the current capture indicative COI (AR interval width 404C) to the baseline CO (AR interval width 404A) at 306. At 318, the processors determine the width 404C is identical to or within a select range of 404A and flow moves to 320. At 320, the current cardiac signals 400C are labeled LOC.

Figure 4D:
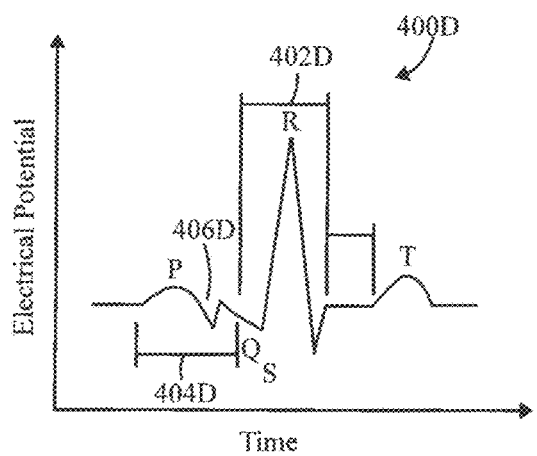
FIG. 4D illustrates a current cardiac signal representative of a NS beat/event in accordance with embodiments herein.

FIG. 4D illustrates a current cardiac signal 400D representative of a NS beat/event, where the current cardiac signal 400D has a QRS complex width 402D that exceeds the baseline QRS width 402A threshold and an activity level 406D in the isoelectric interval that exceeds the activity level (threshold) 406A of the baseline cardiac signal, indicating the presence of delta waves. Together, the ensemble of capture-indicative COI of FIG. 4D compared to the baseline COI of FIG. 4A indicate that the pacing pulses from the LIMD captured both the HIS bundle and the myocardial tissue, achieving non-selective capture.

Examples of cardiac signals representative of intrinsic, selective, and non-selective beat/events may be found in Keene et al., "Rationale and design of the randomized muticentre HIS Optimized Pacing Evaluated for Heart Failure (HOPE-HF) trial: HOPE HF Trial rationale and design," ESC Heart Failure, vol. 5, No. 5, July 2018, DOI: 10.1002/ehf2.12315, and in Teng et al., "Physiological mechanisms of QRS narrowing in bundle branch block patients undergoing permanent HIS bundle pacing," Journal of Electrocardiology, vol. 49, no. 5, September-October 2016, pp. 644-648, which are hereby incorporated by reference in their respective entireties.

With respect to the operations of FIG. 3A, the one or more processors of the SIMD collect and analyze the current cardiac signals 400D at 304, 306. The processors compare the current capture-indicative COI (QRS complex width 402B) to the baseline COI (width 402A) at 306. At 310, the processors determine the width 402B exceeds the baseline COI width 402A and branches to 312. At 306, the processors compare the current capture-indicative COI (level of activity in the isoelectric interval 406D) to the baseline COI (the baseline level of activity of the isoelectric interval 406A). At 312, the processors determine that the current level of activity of the isoelectric interval exceeds the baseline level of activity and branches to 314. At 314, the current cardiac signals 400B are labeled NS capture.

FIG. 3B illustrates a process for binning types of HIS capture events in accordance with embodiments herein.

Subsequent to the one or more processors recording the appropriate label at 324, optionally, flow may continue to FIG. 3B. At 326, the one or more processors of the SIMD bin (maintain a count) labels for a plurality of the events. If the label is determined to be MT-only capture at 328, the one or more processors bin the label in the MT-only capture bin 330, incrementing the total number of MT-Only capture events by one. Flow continues at 326 with the one or more processors of the SIMD continuing to bin labels for a plurality of the events. If the label is determined not to be MT-only capture, the one or more processors proceed to determine if the label is NS capture at 332. If the label is determined to be NS capture at 332, the one or more processors bin the label in the NS capture bin 334, incrementing the total number of NS capture events by one. Flow continues at 326 with the one or more processors of the SIMD continuing to bin labels for a plurality of the events. If the label is determined not to be MT-only capture or NS capture, the one or more processors proceed to determine if the label is HIS-only capture at 336. If the label is determined to be HIS-only capture at 336, the one or more processors bin the label in the HIS-only capture bin 338, incrementing the total number of HIS-only capture events by one. Flow continues at 326 with the one or more processors of the SIMD continuing to bin labels for a plurality of the events. If the label is determined not to be MT-only capture, NS capture, or HIS-only capture, then the one or more processors of the SIMD determine the label to be LOC and bin the label in the LOC bin 340, incrementing the total number of LOC events by one.

At 342, the one or more processors of the SIMD determine if a pre-selected criteria of LOC events is met If the pre-selected criteria of LOC events is not met, the flow returns to 326 with the one or more processors of the SIMD continuing to bin labels for a plurality of the events. If the pre-selected criteria of LOC events are met, the one or more processors transmit LOC information from the SIMD to the LIMD at 344. The pre-selected criterial for the LOC events may include a running total of LOC events since the last time the pre-selected criteria was determined to be met, a select number of LOC events over a select time interval, a select number of LOC events over a select number of beats, and the like. Based on the LOC information, the LIMD may initiate an auto-threshold search to automatically determine capture thresholds for one or more pacing vectors according to embodiments herein. The one or more processors of the SIMD may communicate LOC information to the one or more processors of the LIMD in various manners. For example, the one or more processors of the SIMD may communicate the pre-selected criteria of LOC events to the one or more processors of the LIMD and, optionally, the one or more processors of the LIMD may verify that the pre-selected criteria are met. Additionally, or alternatively, the one or more processors of the SIMD may communicate to the one or more processors of the LIMD that the pre-selected criteria of LOC events has been met. Additionally. or alternatively, the one or more processors of the SIMD may determine that a pre-selected criteria of LOC events is met and communicate an instruction to initiate an auto-threshold search to the one or more processors of the LIMD.

Auto-Threshold Search

Figure 5:
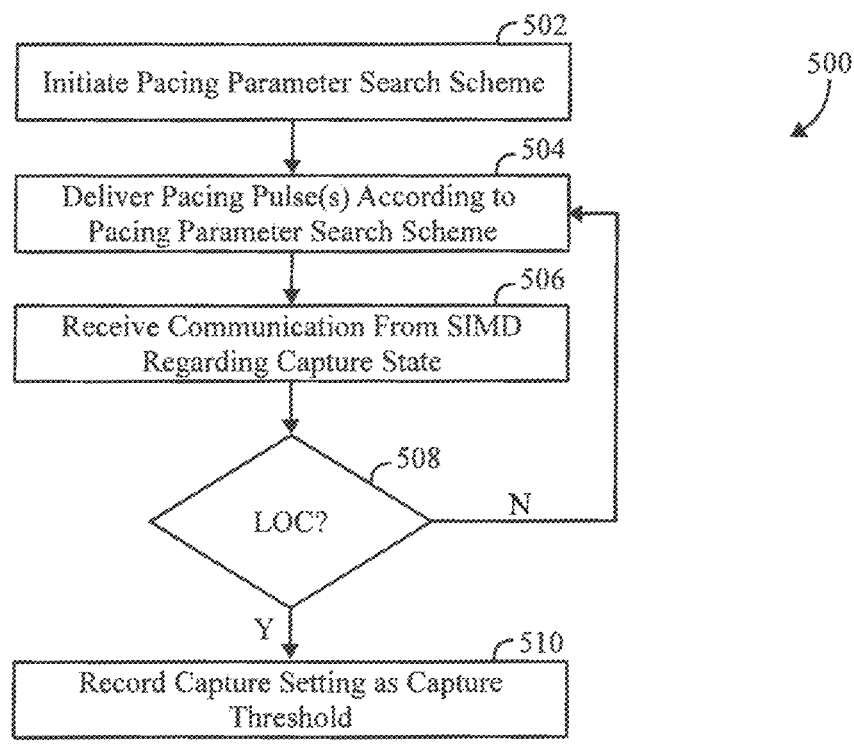
FIG. 5 illustrates a method for automatically determining and adjusting the capture threshold of the LIMD in accordance with embodiments herein.

FIG. 5 illustrates a method 500 for automatically determining and adjusting the capture threshold of the LIMD in accordance with embodiments herein. Adjustment of the capture threshold of the LIMD can include adjusting various pacing parameters such as voltage, pulse width, a number of pulses, pulse shape, and the like. The process begins at 502, where one or more processors of the LIMD initiate a pacing parameter search scheme. The pacing parameter search scheme can be a step-down scheme, a step-up scheme, a binary scheme, or the like, where one or a combination of pacing parameters are adjusted. FIG. 5 illustrates the example of a step down, starting high scheme for determining LOC. However, the same principles apply for other pacing parameter search schemes. During a pacing parameter search scheme for HIS pacing, the transition of the various capture states of HIS pacing may be recorded as the pacing parameters (e.g., pacing amplitudes) are varied.

At 504, the one or more processors of the LIMD cause the LIMD to deliver one or more pacing pulses utilizing stimulation parameters corresponding to an initial step in the pacing parameter search scheme (e.g., a stepped-up or stepped-down voltage compared to voltage of the current capture settings). The one or more processors of the LIMD and/or the SIMD collect/sense the evoked cardiac signals that occur in response to the delivered stimulation pulse(s). The LIMD and/or SIMD analyze the evoked cardiac signals to identify capture-indicative COI, compare the capture-indicative COI to baseline COI to determine if the beat/event corresponds to an LOC event, and communicate the presence or absence of an LOC event to the one or more processors of the LIMD according to the methods of FIGS. 3A and 3B.

At 506, the one or more processors of the LIMD receive communication from the one or more processors of the SIMD regarding the capture state.

At 508, the one or more processors of the LIMD determine whether the communication indicates that evoked cardiac signals were not indicative of loss of capture (e.g., the pacing pulse(s) achieved some other type of capture. Additionally, or alternatively, the communication may contain an instruction to continue to the next step of the pacing parameter search scheme. When the communication indicated no LOC, flow returns to 504. At 504, the one or more processors of the LIMD continue to the next step in the pacing parameter search scheme. For example, when implementing a step-down search scheme, the processors reduce the pacing pulse amplitude by a predetermined voltage step. The operations at 504-508 are repeated until the communication from the SIMD indicates that the evoked cardiac signals indicate that the type of capture corresponds to LOC.

When the one or more processors of the LIMD determines that the communication indicates that evoked cardiac signals were indicative of LOC, flow continues to 510. Additionally, or alternatively, the communication may contain an instruction to cease (or to not continue to the next step of) the pacing parameter search scheme and based thereon flow continues from 508 to 510. At 510, the one or more processors of the LIMD record the capture settings corresponding to the stimulation parameters resulting in the most recent evoked cardiac signals as the new capture threshold.

Figure 6:
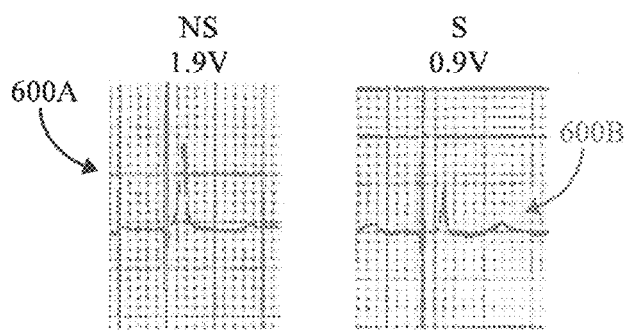
FIG. 6 illustrates one example a first cardiac signal and a second cardiac signal in accordance with the method of FIG. 5 in accordance with embodiments herein.

FIG. 6 represent an example of a step-down pacing parameter search scheme in accordance with embodiments herein. Cardiac signal 600A occurs in response to a first stimulation pulse (e.g., a 1.9V stimulation pulse) in the pacing parameter search scheme of the LIMD. With reference to method 500, the one or more processors of the SIMD determine the current cardiac signal 600A represents a NS capture event and sends a communication to the LIMD indicating the same. At 506, the one or more processors of the LIMD receive the communication from the SIMD indicating that the first stimulation pulse corresponds to a NS capture event (or does not correspond to a LOC event) and flow moves to 504. At 504, the one or more processors of the LIMD cause the LIMD to deliver a second stimulation pulse (e.g., 0.9V) in the pacing parameter search scheme. The one or more processors of the SIMD determine that the current cardiac signal 600B represents a selective capture event and sends a communication to the LIMD indicating the same. The process continues until a LOC event is achieved and recorded at 510.

Closing Statements

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, Including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for monitoring capture within a distributed implantable system comprising:
a first implantable medical device (IMD) comprising:
an electrode configured to be located within a local chamber of a heart; and
circuitry configured to deliver one or more pacing pulses, through the electrode, to the local chamber in connection with an arrhythmia therapy;
a non-transvenous lead having one or more subcutaneous electrodes configured to be located in a non-transvenous parasternal region; and
a second IMD, wherein the second IMD is a subcutaneous IMD (SIMD), the SIMD comprising:
at least one processor;
sensing circuitry coupled to the one or more subcutaneous electrodes of the non-transvenous lead; and
a memory coupled to the at least one processor, the memory configured to store program instructions, wherein the program instructions are executable by the at least one processor to:
utilize the sensing circuitry to collect far field (FF) evoked cardiac signals following the one or more pacing pulses delivered by the first IMD, the sensing circuitry utilizing a sensing vector that extends between one of:
i) two or more subcutaneous electrodes of the non-transvenous lead or
ii) a housing of the SIMD and the one or more subcutaneous electrodes of the non-transvenous lead;

analyze a first capture indicative characteristic of interest (COI) from the FF evoked cardiac signals to identify a first type of capture; and analyze a second capture indicative COI from the FF evoked cardiac signals to identify a second type of capture.

2. The system of claim 1, wherein the first and second types of capture are two of selective capture, myocardial tissue-only (MT-only) capture, or a non-selective (NS) capture.

3. The system of claim 1, wherein the at least one processor is within the second IMD and wherein the program instructions are further executable by the at least one processor to obtain FF baseline cardiac signals and analyze the FF baseline cardiac signals to identify a baseline COI, and wherein the program instructions are further executable by the at least one processor to analyze the FF evoked cardiac signals to distinguish between the first and second types of capture based on the baseline COI and the first and second capture indicative COI.

4. The system of claim 1, wherein, to analyze at least one of the first or second capture indicative COI, the program instructions are further executable by the at least one processor to compare a baseline width of a QRS complex with a QRS width of the FF evoked cardiac signals and compare a baseline level of activity in an isoelectric interval with a level of activity in the isoelectric interval of the FF evoked cardiac signals, and based thereon, label the event as MT-only capture indicating that the one or more pacing pulses from the first IMD captured myocardial tissue only.

5. The system of claim 1, wherein, to analyze at least one of the first or second capture indicative COI, the program instructions are further executable by the at least one processor to compare a baseline width of a QRS complex with a QRS width of the FF evoked cardiac signals and compare a baseline atrial-ventricular (AR) interval to an AR interval of the FF evoked cardiac signals, and based thereon, label the event as loss of capture (LOC) indicating that the one or more pacing pulses from the first IMD did not capture.

6. The system of claim 1, wherein, to analyze at least one of the first or second capture indicative COI, the program instructions are further executable by the at least one processor to compare a baseline width of a QRS complex with a QRS width of the FF evoked cardiac signals and based thereon, label the event as non-selective (NS) capture.

7. The system of claim 1, wherein the program instructions are further executable by the at least one processor to:
bin labels for a plurality of events;
determine when a pre-selected criteria of the events labeled with loss of capture (LOC) is met;
transmit LOC information from the second IMD; and
based on the determined operation, cause the first IMD to initiate an auto threshold search.

8. The system of claim 1, wherein the first IMD is a leadless IMD (LIMD), the LIMD comprising a memory configured to store LIMD program instructions and one or more LIMD processors that, when executing the LIMD program instructions, are configured to receive a communication from the SIMD indicative of a result of the analysis of the FF evoked cardiac signals and to adjust a pacing parameter of the one or more pacing pulses based on the communication.

9. The system of claim 8, wherein the program instructions are further executable by the at least one processor to:
utilize the LIMD to deliver the one or more pacing pulses according to a pacing parameter search scheme,
utilize the SIMD to distinguish between the first and second types of capture for corresponding evoked FF cardiac signals,
utilize the SIMD to transmit capture state information from the SIMD to the LIMD; and
based on the capture state information, determine a pacing parameter.

10. The system of claim 1, wherein the program instructions are further executable by the at least one processor to collect the FF cardiac signals along primary and secondary sensing vectors extending between the housing of the SIMD and the one or more subcutaneous electrodes located at parasternal sensing sites.

11. The system of claim 1, wherein the first IMD represents at least one leadless IMD (LIMD) configured to be implanted in the local chamber proximate to a HIS bundle of the heart, the local chamber representing one of an atrium or ventricle, and wherein the circuitry of the LIMD is configured to deliver the one or more pacing pulses to the electrode at the HIS bundle.

12. The system of claim 1, wherein the first IMD represents at least one leadless IMD (LIMD) configured to be implanted in a septal wall of a right ventricle (RV), the RV representing the local chamber.

13. The system of claim 12, wherein the first IMD is configured to deliver the arrhythmia therapy in the local chamber at a position in the septal wall to treat an arrhythmia associated with bundle branch block.

14. The system of claim 12, wherein the first IMD is configured to deliver the arrhythmia therapy in the local chamber at a position in the septal wall to electrically resynchronize ventricular activation in left and right bundle branches.

15. The system of claim 1, wherein the first IMD is configured to deliver, as the arrhythmia therapy, at least one of a pacing therapy, cardiac resynchronization therapy (CRT), or anti-tachycardia pacing therapy.

16. The system of claim 1, wherein the first IMD represents at least one leadless IMD (LIMD) and is configured to deliver anti-tachycardia pacing therapy, and wherein the SIMD is configured to deliver a defibrillation therapy.

17. The system of claim 1, wherein the first IMD is configured to detect an arrhythmia, the circuitry of the first IMD configured to deliver the one or more pacing pulses in connection with treating the arrhythmia.

18. The system of claim 1, wherein the one or more pacing pulses are defined by pacing parameters associated with the arrhythmia therapy but are delivered by the first IMD during at least one of a threshold search or capture detection process.

19. The system of claim 1, wherein the SIMD is coupled to subcutaneous electrodes positioned outside of the heart, the sensing circuitry coupled to the subcutaneous electrodes and configured to collect the FF evoked cardiac signals.

20. A computer implemented method for monitoring capture within a distributed implantable system having first and second implantable medical devices (IMDs), wherein the first IMD comprises circuitry and an electrode configured to be located within a local chamber of a heart, wherein the second IMD is a subcutaneous IMD (SIMD) having one or more processors, a non-transvenous lead having one or more subcutaneous electrodes configured to be located in a non-transvenous parasternal region, and sensing circuitry, the method comprising:
utilizing the circuitry, of the first IMD, to deliver one or more pacing pulses, through the electrode, to the local chamber in connection with an arrhythmia therapy;

under control of the one or more processors, of the SIMD, configured with program instructions, utilizing the sensing circuitry for collecting far field (FF) evoked cardiac signals following the one or more pacing pulses delivered by the first IMD, the sensing circuitry utilizing a sensing vector that extends between one of:
- i) two or more subcutaneous electrodes of the non-transvenous lead or
- ii) a housing of the SIMD and the one or more subcutaneous electrodes of the non-transvenous lead;

analyzing a first capture indicative characteristic of interest (COI) from the FF evoked cardiac signals to identify a first type of capture; and analyzing a second capture indicative COI from the FF evoked cardiac signals to identify a second type of capture.

21. The method of claim 20, wherein the first and second types of capture are two of selective capture, myocardial tissue-only (MT-only) capture, or a non-selective (NS) capture.

22. The method of claim 20, wherein the first IMD is a leadless IMD (LIMD) that comprises a memory configured to store LIMD program instructions and one or more LIMD processors configured to execute the LIMD program instructions, the method further comprising, under control of the one or more LIMD processors:

receiving, at the LIMD, a communication from the SIMD indicative of a result of the analysis of the FF evoked cardiac signals; and adjusting a pacing parameter of the one or more pacing pulses based on the communication.

23. The method of claim 20, further comprising utilizing the SIMD for obtaining FF baseline cardiac signals, analyzing the FF baseline cardiac signals to identify a baseline COI, and distinguishing between the first and second types of capture based on the baseline COI.

24. The method of claim 20, wherein the electrode of the first IMD is configured to be located at, and to deliver the pacing pulses to, a HIS bundle, and wherein the analyzing further comprises identifying the first and second types of capture as first and second types of HIS capture based on a baseline COI and first and second capture indicative COI of the FF evoked cardiac signals.

25. The method of claim 20, wherein the first IMD represents at least one leadless IMD (LIMD) configured to be implanted in the local chamber proximate to a HIS bundle of the heart, the local chamber representing one of an atrium or ventricle.

26. The method of claim 20, wherein the first IMD represents at least one leadless IMD (LIMD) configured to be implanted in a septal wall of a right ventricle (RV), the RV representing the local chamber.

27. The method of claim 26, wherein the first IMD is configured to be deliver the arrhythmia therapy in the local chamber at a position in the septal wall to treat an arrhythmia associated with bundle branch block.

28. The method of claim 26, wherein the first IMD is configured to be deliver the arrhythmia therapy in the local chamber at a position in the septal wall to electrically resynchronize ventricular activation in left and right bundle branches.

29. The method of claim 20, the method further comprising delivering, as the arrhythmia therapy, at least one of a pacing therapy, cardiac resynchronization therapy (CRT), or anti-tachycardia pacing therapy.

30. The method of claim 20, wherein the first IMD represents at least one leadless IMD (LIMD), the method further comprising: delivering an anti-tachycardia pacing therapy by the LIMD, and delivering a defibrillation therapy by the SIMD.

31. The method of claim 20, further comprising: detecting an arrhythmia, and delivering the one or more pacing pulses in connection with treating the arrhythmia.

32. The method of claim 20, wherein the one or more pacing pulses are defined by pacing parameters associated with the arrhythmia therapy, the method further comprising delivering the one or more pacing pulses during at least one of a threshold search or capture detection process independent of whether the heart is experiencing an arrhythmia.

33. The method of claim 20, wherein the SIMD is coupled to subcutaneous electrodes positioned outside of the heart, the sensing circuitry coupled to the subcutaneous electrodes and configured to collect the FF evoked cardiac signals.

* * * * *